United States Patent [19]

Falcone, Jr.

[11] Patent Number: 4,781,809
[45] Date of Patent: Nov. 1, 1988

[54] RECOVERING FREE ORGANIC ACIDS FROM SOLUTIONS IN WHICH THEY OCCUR WITH OTHER ORGANIC MATTER

[75] Inventor: John L. Falcone, Jr., Watertown, Mass.

[73] Assignee: Ionics, Incorporated, Watertown, Mass.

[21] Appl. No.: 887,668

[22] Filed: Jul. 21, 1986

[51] Int. Cl.$^4$ ............................................. B01D 13/02
[52] U.S. Cl. .............................. 204/182.4; 204/182.6; 204/186; 204/301; 204/302; 426/239
[58] Field of Search .................. 204/301, 182.3, 182.4, 204/182.6, 302, 186; 426/239

[56] References Cited

U.S. PATENT DOCUMENTS

| | | | |
|---|---|---|---|
| 3,165,415 | 10/1960 | Kilburn et al. | 204/182.4 |
| 3,654,125 | 8/1968 | Leitz | 204/182.4 |
| 3,878,086 | 4/1975 | Haswell et al. | 204/301 |
| 4,024,043 | 5/1977 | Dege et al. | 204/182.4 |
| 4,057,483 | 11/1977 | Giuffrida | 204/182.4 |
| 4,110,175 | 8/1978 | Ahlgren et al. | 204/301 |
| 4,632,745 | 12/1986 | Giuffrida et al. | 204/301 |

FOREIGN PATENT DOCUMENTS 59-143574  8/1984  Japan .................................. 426/239

Primary Examiner—John F. Niebling
Assistant Examiner—Ben C. Hsing
Attorney, Agent, or Firm—Norman E. Saliba

[57] ABSTRACT

Processes and apparatus are disclosed for recovering free organic acids from aqueous solutions in which they occur at least in part as free acid together with other organic matter comprising:

(a) passing said solution through a de-acidifying chamber (compartment, cell, space) in an electrodialysis ("ED") apparatus, said de-acidifying chamber defined on each face thereof by membranes substantially permeable to anions, said membranes separated from each other by turbulence promoting spacers, such ED apparatus also comprising an organic acid receiving chamber juxtaposed to one face of said de-acidifying chamber;

(b) passing a direct electric current (which may include alternating current components) through said ED apparatus in a direction to cause anions of said organic acid and hydronium cations to migrate into said organic acid receiving chamber; and (c) recovering from said organic acid receiving chamber a solution comprising free organic acid.

4 Claims, 1 Drawing Sheet

RECOVERING FREE ORGANIC ACIDS FROM SOLUTIONS IN WHICH THEY OCCUR WITH OTHER ORGANIC MATTER

BACKGROUND OF THE INVENTION

1. Field of the Invention

It is well known that fruit juices (including tomato juice) and their fermentation products (e.g. grape wine and apple cider) contain substantial quantities of organic acids at least part in the free form. For example, the juice of citrus fruits, pineapples and tomatoes contain citric acid as the principal organic acid; in grape juice and grape wine the principal organic acid is tartaric acid (present as the acid potassium salt); and in apple juice and apple cider the principal organic acid is malic acid. In addition, fruit juice typically has a small amount of succinic acid. It is often desirable to recover free, preferably food-grade, organic acids from said juices, for example, when there is an excess of fruit for food-use, when the end-use can tolerate some removal of organic acids or when the organoleptic, storage and/or processing characteristics of the juice will be improved by partial removal of such acids. In the latter two cases, of course, it is imperative that the food and organoleptic values of the juice should not be impaired for the intended end-use.

It is also well-known that organic acids are produced together with other organic matter by fermentation of suitable substrates with appropriate microorganisms. Typically the organic acids have not been recovered directly as free acid from such fermentations but rather in the form of their calcium, sodium, ammonium or potassium salts. It is often desirable as well to recover free organic acids directly from such fermentations.

Illustrative organic acids include:

Citric acid (i.e., 2-hydroxy-1,2,3-propane tricarboxylic acid, $C_6H_8O_7$, molecular weight about 192.13), which occurs abundantly in citrus fruits, e.g. lemons (4 to 8%), grapefruit (1.2 to 2.1%), tangerines (0.9 to 1.2%), oranges (0.6 to 1.0%) and limes (about 7%). It is also made by certain strains of Aspergillus niger grown on the surface of sucrose-and-salt solutions; by a submerged fermentation process using the same microorganism; by submerged fermentation of either glucose or molasses with an equivalent amount of sugar by species of yeasts (for example, Candida guilliermondii); by fermentation of purified, liquid, normal paraffins by other species of yeast (for example, Candida lipolytica). Citric acid is generally recovered from a fermented aqueous solution by first separating the microorganisms and then precipitating the citrate ion as the insoluble calcium salt to separate fermentation by-products and other impurities from the citrate ion. Acidification with sulfuric acid converts calcium citrate to citric acid and insoluble calcium sulfate. The resulting solution of crude citric acid is concentrated and filtered to remove calcium sulfate and finally repeatedly crystallized to remove other impurities.

A more modern process uses liquid extraction, activated carbon and multiple recrystallization to recover citric acid.

Electrolysis has been used on a pilot scale to recover citric acid and sodium hydroxide from monosodium acid citrate solution.

Citric acid is used in cosmetics as a buffer to control pH in shampoos, hair rinses and setting lotions. It is also used extensively in food and pharmaceutical products as well as in many industrial applications.

Lactic acid (2-hydroxy propionic acid, $C_3H_6O_3$, molecular weight about 90.08) is made by fermentation of carbohydrates (e.g. sucrose, lactose, cheese whey) by *Lactobacillus delbrueckii, L. bulgaricus* or *L. leichmanii*. Primary uses are in foodstuffs and pharmaceutical products in which it has a mild acidic taste in contrast with the sharp taste of some of the other food acids. Lactic acid may be recovered from the above mentioned fermentations by crystallization of calcium lactate followed by conversion of the latter to lactic acid with sulfuric acid. Lactic acid can also be recovered by anion exchange. The latter process suffers from fouling of the exchange resin, production of a waste sodium sulfate stream and the cost of sodium hydroxide and sulfuric acid needed for regeneration of the exchange resin.

Tartaric acid (2,3-dihydroxy succinic acid, $C_4H_6O_6$, molecular weight about 150.09) occurs in the dextrorotary form as potassium hydrogen tartrate ("cream of tartar") in grape juice, wine and wine by-products. Classically the insoluble calcium tartrate has been used to separate tartrate from impurities. Acidification with sulfuric acid is then used to convert calcium tartrate back to tartaric acid, followed by concentration and filtration to remove calcium sulfate. Repeated recrystallization yields pure tartaric acid. The latter is used as an acidulant in carbonated and still beverages including beverage powders as well as in other acidulated food products.

Malic acid (hydroxy succinic acid, $C_4H_6O_5$, molecular weight about 134.09) occurs in apple juice as the levorotary form. It is used in food applications (for example, hard candy) because of its pleasant tartness and flavor-retention characteristics and in non-food applications because of its high solubility in water and its chelating and buffering properties.

Succinic acid ($C_4H_6O_4$, molecular weight about 118.09) occurs with other organic carboxylic acids in most fruit juices. It is used as a flavor enhancer and preservative, as a pH control agent in condiments and relishes, in meat products, in medicinals and in cosmetics.

It will be seen that the five above mentioned organic acids have substantial uses in food products, medicinals and cosmetics and that therefore it is preferable if such acids for such uses are derived from natural sources rather than by synthetic means.

It is therefore an objective of this invention to provide processes and apparatuses for economically recovering free organic acids from aqueous solutions or suspensions in which they occur at least in part as free acid together with other organic matter. It is also an objective to recover such acids from fruit juices (including tomato juices), concentrates thereof or fermentation products thereof without substantially impairing the organoleptic value or the processing and storage characteristics of said juice or derivative thereof.

These objectives and others will become clear from the following description, drawings, examples and claims.

2. Description of the Prior Art

Kilburn et al. (U.S. Pat. No. 3,165,415) describe the recovery of sodium citrate containing excess caustic by Donnan (Exchange) Dialysis or Electrodialysis ("ED") of citrus juices against caustic solutions using anion selective membranes. The repeating units in the apparatus consist of two compartments and alkali is fed to every other compartment. More details of the processes are given by R. N. Smith et al. in "Electrodialysis Processing of Citrus Juice", presented at the Research and Development Associates, Convenience Foods Conference, Philadelphia, Pa., Nov. 18, 64 and by W. K. W. Chen, Kirk-Othmer Encyclopedia of Chemical Technology, John Wiley and Sons, Inc., N.Y., 1965, Vol. 7 page 861. The feed citrus juice typically contained 12 grams soluble solids per 100 grams juice (12 Brix) and 1 gram acidity expressed as anhydrous citric acid per 100 ml of juice. The effluent juice was typically 12 Brix with an acidity of 0.8 grams per 100 ml in the same units. The citrate was recovered in a substantial excess of caustic potash. The high level of pectins and other organic materials present in the juice caused a rapid increase in electrical resistance of the all anion membrane electrodialysis stack. To solve this problem, reversal of the electric current was effected every few minutes without interchanging the juice and caustic potash streams. The superstoichiometric use of expensive caustic potash made this process uneconomical.

As pointed out above, lactic, citric and tartaric acids have been recovered classically in multi-step processes involving precipitation of the calcium salts, resolubilizing with sulfuric acid, multiple recrystallization and purification steps, the latter often with activated carbon and/or ion-exchange. Citric acid has also been recovered on a pilot scale by multiple recrystallizations of its monosodium salt followed by electrolysis of the latter to sodium hydroxide and free acid. Alanine and tartaric acid have been recovered by similar processes. These processes cannot be applied to the recovery of organic acids from fruit juices or fermentation products thereof without seriously interfering with the organoleptic, food and processing values of the juice or fermentation product thereof.

DESCRIPTION OF PREFERRED EMBODIMENTS

In its broadest aspect, the present invention comprises processes and apparatus for recovering free organic acids from aqueous solutions in which they occur substantially as free acid together with other organic matter comprising:

(a) preferably clarifying said aqueous solution;

(b) passing said clarified solution through a de-acidifying chamber (compartment, cell, space) in an electrodialysis ("ED") apparatus, said deacidifying chamber defined on each face thereof by membranes substantially permeable to anions, said membranes separated from each other by turbulence promoting spacers, such ED apparatus also comprising an organic acid receiving chamber juxtaposed to one face of said de-acidifying chamber;

(c) passing a direct electric current (which may include alternating current components) through said ED apparatus in a direction to cause anions of said organic acid and hydrogen ions to migrate into said organic acid receiving chamber;

(d) recovering from said organic acid receiving chamber a solution comprising free organic acid; and (e) recovering from said de-acidifying chamber solution depleted in said organic acid.

Figure 1:
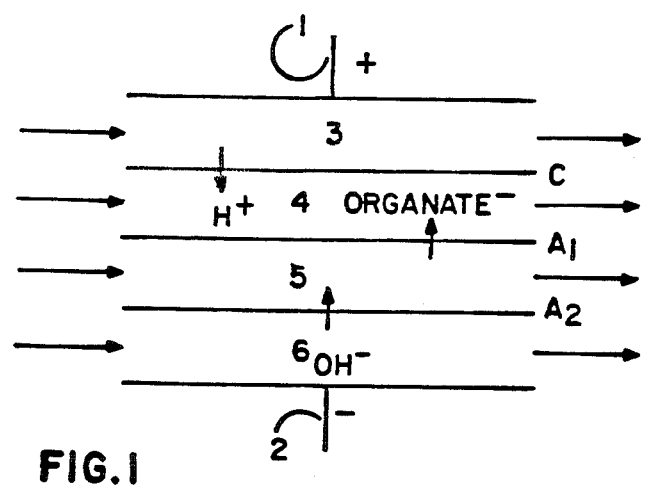
FIG. 1 is a schematic representation of a preferred simple electrodialysis apparatus for recovering free organic acid from solutions thereof together with other organic matter.

Referring to FIG. 1, there is indicated schematically a preferred simple ED apparatus for carrying out the process of this invention comprising a positive electrode 1 (anode), a cation-selective membrane C spaced therefrom, two anion-selective membranes $A_1$, $A_2$ spaced from each other, from the cation-selective membrane and from a negatively charged electrode 2 (cathode). The anode and spaced adjacent cation-selective membrane C define therebetween an anode or anolyte chamber 3 (compartment, cell, space); the cation-selective membrane C and adjacent but spaced anion-selective $A_1$ membrane define therebetween an organic-acid-receivingchamber 4, the two spaced anion-selective membranes $A_1$ and $A_2$ define therebetween a deacidifying chamber 5; and the cathode 2 and adjacent spaced anion-selective $A_2$ membrane define therebetween a cathode or catholyte chamber 6. There are provided: means for introducing an acidic solution into said anolyte chamber 3 and means for removing said acidic solution typically mixed with oxygen gas from said chamber; means for introducing an alkaline solution into said catholyte chamber 6 and means for removing said alkaline solution typically mixed with hydrogen gas from said chamber; means for introducing a substantially clear solution of said organic acid together with other organic matter into said de-acidifying chamber 5 and means for removing and recovering said solution at least partially de-acidified from said chamber; and generally means for introducing an organic acid receiving liquid such as water into said organic acid receiving chamber 4 and means for removing and recovering liquid enriched in said organic acid from said organic acid receiving chamber.

Adjacent membranes and electrodes are typically spaced from each other by distances in the range of from about 0.020 to about 0.080 inches. The space between the two anion-selective membranes $A_1$ and $A_2$ preferably contains structure to promote mass transfer in the de-acidifying chamber 5 at least toward the anion-selective membrane $A_1$ bordering said chamber on the anode face thereof. Such structure may comprise: a tortuous path spacer with frequent (e.g. every ¾ or ½ inch) eddy-promoting cross-straps; woven or nonwoven screen; a perforated, corrugated spacer; all as well known in the ED art. The cathode 2 and anode 1 may take the form for example of sheets, expanded sheets, perforated sheets, perforated and corrugated sheets, woven mesh, wires and the like. The material of construction of the cathode and anode may be any material well-known in the art, for example, graphite, nickel, austenitic stainless steel (e.g. type 316), Incology 825, Hastelloy C-276, Inconel 600 or titanium, zirconium, niobium or tantalum or their alloys (e.g. Grade VII titanium) coated or plated with one or more platinum group metals and/or oxides thereof.

The ion-selective membranes may be any well-known in the art. Particularly preferred for the anion selective membranes $A_1$ bounding the de-acidifying chamber 5 on the anode face thereof are: anion-selective membranes having a low Hittorf transport number for hydrogen ions in acid solutions such as for example Type AAV of Asahi Glass Co., Tokyo, Japan; fouling-resistant anion-selective membranes such as type AR204SXZL of Ionics, Inc., Watertown, Massachusetts, U.S.A. and types AFN and ACLE-5P of Tokuyama Soda Co., Tokuyama City, Japan; and anion-selective membranes having fixed negatively charged groups on the surface such as type ACS of Tokuyama Soda.

The apparatus also includes means for applying a direct electric current between said positive and said negative electrode (1 and 2 respectively). As a result of said current:

(a) organic acid anions ("organate" ions) are transferred from said de-acidifying chamber 5 through the anion permeable membrane $A_1$ on the anode face thereof into the organic acid receiving chamber 4 to the substantial exclusion of transfer of non-ionized moieties;

(b) hydrogen ions ($H^+$) or their equivalent hydronium ions ($H_3O^+$) are transferred from the anolyte chamber 3 through the adjacent cation selective membrane C into the organic acid receiving chamber 4 where they are associated with the organate ions as substantially free organic acid;

(c) water is decomposed at the anode 1, thereby replenishing the $H^+$ (or $H_3O^+$) ions in the anolyte chamber 3 and forming $O_2$ gas (typically) which exits the anolyte chamber with the acidic solution. After separating said $O_2$ gas, and optionally cooling the acid it is generally recycled to the entrance means of the anolyte chamber. The cation-selective membrane C separating the anolyte chamber 3 from the organic acid receiving chamber 4 inhibits the transfer of anions from the anolyte chamber into the organic acid receiving chamber. As a result there is substantially no makeup of acid, no cost thereof and no cost for disposal of anions transferred through the cation-selective membrane;

(d) hydroxide ions ($OH^-$) are transferred from the catholyte chamber 6 through the adjacent anion selective membrane $A_2$ into the de-acidifying chamber 5 replacing the organate anions which have moved to the organic acid receiving chamber;

(e) water is decomposed at the cathode 2 thereby replenishing the $OH^-$ ions in the catholyte chamber and forming $H_2$ gas (typically) which exits the catholyte chamber with the alkaline solution. After separating said $H_2$ gas and optionally cooling the alkali it is generally recycled to the entrance means of the catholyte chamber. The anion-selective membrane $A_2$ separating the catholyte chamber 6 from the de-acidifying chamber 5 inhibits the transfer of cations from the catholyte chamber into the de-acidifying chamber. As a result there is substantially no makeup of alkali, no cost thereof and no cost for disposal of cations transferred through the anion-selective membrane.

The direction of the direct electric current may be reversed periodically for short periods of time (e.g. for one minute every 15 minutes) to help avoid fouling of the anion-selective membrane $A_1$ between the de-acidifying and organic acid receiving chambers (5 and 4 respectively).

In a particularly preferred apparatus, either or both of the electrodes are foraminous and partially imbedded in the surface of (or otherwise in intimate contact with) the adjacent ion-selective membrane. In such case the respective acid or alkali is not required. At such composite anode, water is decomposed to $H^+$ ($H_3O^+$) ions which pass into the organic acid receiving chamber 4 and typically $O_2$ gas which exits the anolyte chamber 3. At such composite cathode water is decomposed to $OH^-$ ions which pass into the de-acidifying chamber 5 and typically $H_2$ gas which exits the catholyte chamber 6.

Figure 2:
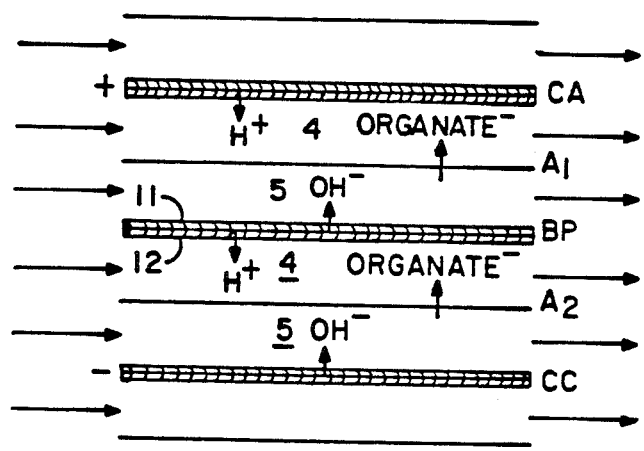
FIG. 2 is a schematic representation of another preferred simple electrodialysis apparatus for recovering free organic acid, said apparatus comprising composite membrane-electrodes and bipolar water-splitting membranes.

Referring to FIG. 2, there is indicated schematically a particularly preferred simple ED apparatus for carrying out the process of this invention comprising: a positive composite membrane electrode (composite anode, CA) spaced from a first anion-selective membrane $A_1$ thereby forming a first organic acid receiving chamber 4 therebetween; a bipolar membrane BP spaced from said anion-selective membrane $A_1$ thereby forming a first de-acidifying chamber 5 therebetween, the anion-selective region 11 of said bipolar membrane BP facing said first de-acidifying chamber 5; a second anion-selective membrane $A_2$ spaced from the cation-selective region 12 of said bipolar membrane BP thereby forming a second organic acid receiving chamber 4 therebetween; and a negative composite membrane electrode (composite cathode, CC) spaced from said second anion-selective membrane $A_2$ thereby forming a second de-acidifying chamber 5 therebetween. The operation of the composite electrodes, suitable anion-selective membranes and suitable mass-transfer promoting structures for the de-acidifying chamber have been described above in connection with FIG. 1. Suitable bipolar membranes are described in U.S. Pat. Nos. 2,829,095, 3,562,139 and 4,057,481; by Frilette (J. Phys. Chem. 1956, vol. 60, p. 435 et seq); and by Glueckauf et al. (J. Appl. Chem. 1956, vol. 6, p. 511 et seq). They are sometimes described as water-splitting membranes since when a direct electric current is applied in a direction to cause anions to migrate through the anion-selective region away from the junction of the anion- and cation-selective regions (11 and 12 respectively) of the bipolar membrane, then at steady state $OH^-$ and $H^+$ ($H_3O^+$) ions from the dissociation of water migrate away from said junction through the anion- and cation-selective regions respectively.

Electrodialysis apparatus having many de-acidifying chambers and an essentially equal number of organic acid receiving chambers similar to that indicated schematically in FIG. 2 may be constructed by including between a single pair of composite membrane-electrodes many repeating units each comprising: an organic acid receiving chamber; on the anode side thereof a bipolar membrane, the cation-selective region of which faces said organic acid receiving chamber; on the anode side of the bipolar membrane a de-acidifying chamber; and on the anode side thereof an anion-selective membrane. Such apparatus produces gases ($O_2$ and $H_2$) only at the end composite electrodes and no requirement for extraneous alkali or acid (other than the clear organic-acid-plus-organics solution fed to the de-acidifying chambers and the organic acid solution which is typically recirculated through the organic acid receiving chambers).

The direction of the electric current may be reversed periodically for short periods of time (e.g. for one minute every 15 minutes) to help avoid fouling of the anion-selective membranes between the de-acidifying and the organic receiving chambers).

Figure 3:
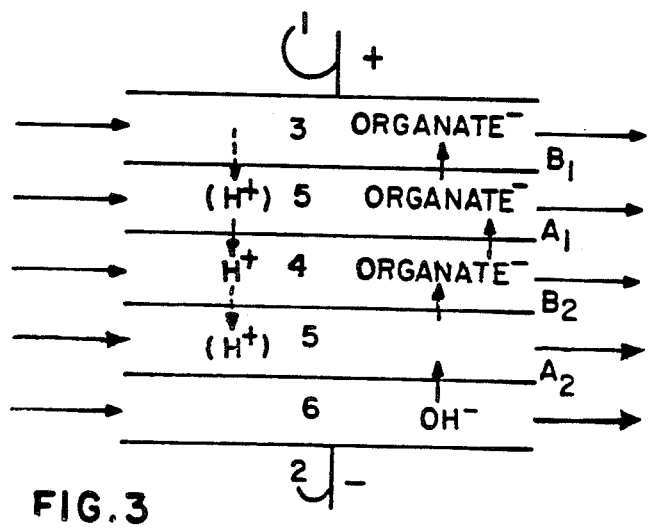
FIG. 3 is a schematic representation of a third preferred simple electrodialysis apparatus for recovering free organic acid, said apparatus comprising "normal" anion-selective membranes and anion-selective membranes which have a low transport number for hydrogen ions in acid solutions.

Referring to FIG. 3, there is indicated schematically a particularly preferred simple ED apparatus for carrying out the process of this invention comprising: a positive electrode (anode) 1, a first anion-selective membrane $B_1$ having a low Hittorf transport number for $H^+$ ($H_3O^+$) ions in acid solution spaced therefrom defining therebetween an anolyte chamber 3 (which is also an organic acid receiving chamber); spaced from said anion-selective membrane $B_1$ in the direction of the negative electrode 2 a first normal anion-selective membrane $A_1$ forming therewith a first de-acidifying chamber 5; spaced from said anion-selective membrane $A_1$ in the direction of the negative electrode a second anion-selective membrane ($B_2$) having a low Hittorf transport number for $H^+$ ($H_3O^+$) ions in acid solution defining therebetween a second organic acid receiving chamber 4; spaced from said anion-selective membrane $B_2$ in the direction of the negative electrode 2 a second normal anion-selective membrane ($A_2$) forming therewith a second de-acidifying chamber 5; and spaced from anion-selective membrane $A_2$ a negative electrode (cathode) 2 forming therewith a catholyte chamber 6. ED apparatus in accordance with FIG. 3 but having many de-acidifying chambers and essentially an equal number of organic acid receiving chambers between a single pair of end electrodes may be constructed by including many repeating units each comprising: an organic acid receiving chamber; on the cathode side thereof a normal anion-selective membrane; on the cathode side of the latter a de-acidifying chamber; and on the cathode side of said de-acidifying chamber an anion-selective membrane having a low Hittorf transport number for $H^+$ ($H_3O^+$). Suitable electrodes, normal anion-selective membranes and mass transport promoting structures for the de-acidifying chambers have been described in connection with the above discussions of FIGS. 1 and 2. (It will be obvious to those skilled in the art that the apparatus schematized in FIG. 3 may be easily modified to utilize composite membrane-electrodes as the end electrodes.) Suitable anion-selective membranes $B_1$, $B_2$ having low $H^+$ ($H_3O^+$) Hittorf transport numbers in acid solution include type AAV of Asahi Glass Company, Tokyo, Japan. When a direct electric current (which may have a substantial alternating current component) is applied between the electrodes, $H^+$ ($H_3O^+$) ions from the de-acidifying chambers will be transferred across the normal anion-selective membranes $A_1$ and $A_2$ (which have a substantial Hittorf transport number for $H^+$ ($H_3O^+$) ions)) into the organic acid receiving compartments 4 (except of course at the cathode where $OH^-$ ions will transfer into the adjacent de-acidifying chamber 5, equivalent in principle to $H^+$ ($H_3O^+$) ions leaving said chamber). Simultaneously anions of the organic acid (organate ions) from the de-acidifying chambers 5 will be transferred across the anion-selective membranes B which have low Hittorf transport number for $H^+$ ($H_3O^+$) ions into the organic acid receiving chambers 4. It will be clear to those skilled in the art that the normal anion-selective membranes A will also transport some organate ions and the anion-selective membranes B having a low $H^+$ ($H_3O^+$) Hittorf transport number will nevertheless transport some $H^+$ ($H_3O^+$). Nevertheless there will be a net transport of organic acid from the de-acidifying chambers to the organic acid receiving chambers. The advantage of the apparatus of FIG. 3 is that both types of anion-selective membranes (A and B) have low transport numbers for metallic cations (such as $Na^+$ or $K^+$) and organic acid can be recovered from the organic acid receiving compartments in relatively pure form.

The direction of the electric current may be reversed periodically for short periods of time (e.g. for one minute every 15 minutes without interchanging the flows to the de-acidifying and organic acid receiving chambers to minimize fouling of the anion-selective membranes between the de-acidifying chambers and the organic acid receiving chambers. Alternatively the direction of the electric current may be more or less symmetrically reversed, e.g. passing for about half an hour in one direction and then for about the same length of time in the opposite direction. An inspection of FIG. 3 will show that when the direction of the direct current is reversed a former de-acidifying chamber becomes an organic acid receiving chamber while a former organic acid receiving chamber becomes a de-acidifying chamber. The flow of, for example, clarified fruit juice which had been introduced into the former de-acidifying chambers must therefore be diverted (switched) to new de-acidifying chambers and the flow of organic acid receiving solution must be changed to the new organic acid receiving chambers. Such interchange is practical since the solutes in the organic acid receiving stream were all derived from the clarified fruit juice (for example) and there is no sweetening-on-sweetening-off problem such as would be encountered by symmetrical reversal of apparatus known in the art, for example, that of Kilburn et al.

EXAMPLE 1:

Part I: Pasteurized, fresh, sweet cheddar cheese whey is clarified by centrifugation or cross-flow filtration and then about 50 percent of the ash is removed by electrodialysis ("ED") in a 20 cell pair laboratory electrodialysis stack in demineralization mode available from Ionics, Inc., Watertown, Massachusetts, U.S.A. (The stack uses 9 by 10 inch low density polyethylene tortuous path spacers having thicknesses of about 0.040 inches, flow path length of about 137 inches and effective transfer areas of about 35.5 square inches. The membranes are Ionics' CR61CZL386 cation selective membranes and AR103QZL386 anion selective membranes.) The thus partially deashed whey is further deashed by passing first through 10 to 12 percent cross-linked macroporous polystyrene sulfonate cation exchange resin in the hydrogen form and then through macroporous acrylic-based weakly basic amine anion exchange resin in the free base form. The overall ash removal by ED and ion-exchange is about 90 to 95 percent. The clear, deashed whey is fermented at about 44° C. using a mixed culture of Streptococcus *thermophilus* and *Lactobacillus bulgaricus*.

Part II: The pH of the fermentation bath is maintained at about 5.5 by continuously withdrawing a sidestream from the fermenter and sending it through a cross-flow filter. The retentate is recycled to the fermenter. The permeate is passed to a laboratory electrodialysis stack similar to that shown schematically in FIG. 1. Each repeating unit consists of a platinized niobium anode 1, an 0.080 inch thick tortuous path spacer defining an anode chamber 3, a CR61CZL386 cation-selective membrane $C_1$, a 0.040 inch thick tortuous path spacer defining an organic acid receiving chamber 4, an AR103QZL386 anion-selective membrane $A_1$, a second 0.040 inch thick tortuous path spacer defining a de-acidifying chamber 5, a second AR103QZL386 anion-selective membrane $A_2$, a second 0.080 inch thick tortuous path spacer defining a cathode chamber 6, and a type 316 austenitic stainless steel cathode 2. The spacers have available areas of about 35.5 square inches and flow path lengths of about 137 inches. The cross-flow filtrate is passed through the deacidifying chamber 5 in each repeating unit (that is, between the anion-selective membranes) at a flow rate of about 12 inches per second. Sodium hydroxide solution having a concentration of about 2 percent by weight is passed through the cathode chambers 6 and sulfuric acid having a concentration of about 2.5 percent is passed through the anode chambers 3. An unfiltered direct current having about 5 percent ripple is applied between the electrodes at a current density less than the polarizing current density of the de-acidifying chamber. The flow through the organic acid receiving chamber 4 in each repeating unit (that is between the cation-selective membrane C and the anion-selective membrane $A_1$) is also about 12 inches per second and is recirculated through said chamber. Water is added to the recirculating organic acid receiving stream to maintain the concentration of lactic acid in that stream at about 10 percent by weight. About 50 percent of the lactate is removed from the cross-flow filtrate by such ED and such acid depleted solution is returned to the fermenter. Free lactic acid is recovered from the recirculating organic acid receiving stream. It is found that there are no substantial losses of sodium hydroxide from the catholyte or of sulfuric acid from the anolyte. Hence the costs of sodium hydroxide and sulfuric acid and the cost of disposing of waste sodium sulfate have been minimized compared to other processes known in the prior art.

EXAMPLE 2:

Frozen grapefruit juice concentrate is reconstituted with water and divided into substantially equal parts of clear cross-flow filtrate and suspended solids retentate by cross-flow filtration. The cross-flow filtrate is passed through the de-acidifying chambers 5 of the apparatus of Example 1, Part II at a velocity in the range of from about 6 to about 10 inches per second. The flow to the cathode chambers is about 2.8 percent potassium hydroxide and to the anode chambers about 2.5 percent sulfuric acid. A current density of about 0.2 amperes per square inch is applied and about half the acidity is removed from the cross-flow filtrate. Make-up water to the organic acid receiving chamber 4 is adjusted to maintain about 10 percent citric acid in the recirculating organic acid receiving stream. Citric acid is recovered from the organic acid receiving chambers. Partially deacidified grapefruit juice serum is recovered from the de-acidifying chambers of the electrodialysis apparatus and mixed with the above mentioned suspended solids retentate. The resulting product tastes sweeter (less tart) than the original reconstituted grapefruit juice and is free of any salt taste. It is found that there are no substantial losses of potassium hydroxide from the catholyte or of sulfuric acid from the anolyte. Hence the costs of potassium hydroxide and the cost of disposal of waste products have been minimized compared to other processes for recovering citric acid from citrus juices known in the prior art.

EXAMPLE 3:

The ED apparatus of Example 1, Part 1 is converted to the organic acid recovery apparatus of FIG. 3 by replacing the AR103QZL386 anion-selective membranes and the CR61CZL386 cation-selective membranes of the apparatus respectively with Type AAV and Type AMV anion-selective membranes available from Asahi Glass Co., Tokyo, Japan. Type AAV membrane (B) has a low transport number for hydrogen ions in acid solutions. Grapefruit juice crossflow filtrate, prepared as in example 2 is passed through the de-acidifying chambers 5 of the resulting apparatus (said chambers defined by having AAV membranes (B) on the anode side and AMV membranes (A) on the cathode side) at a velocity of about 15 inches per second. A direct current voltage of about 1 volt per membrane (plus the voltage drop of the electrodes) is applied. The temperature is controlled in the range of from about 30° to about 40° C. About half the acidity is removed from the grapefruit juice serum. The organic acid receiving stream 4 (i.e. that in chambers 4 defined by having AAV membranes (B) on the cathode side and AMV membranes (A) on the anode side) is recirculated at about 15 inches per second also. Water is added to maintain the citric acid concentration at about 10 percent. Citric acid is recovered from the organic acid receiving chambers. It is relatively free from metallic cations. Partially de-acidified grapefruit juice serum is recovered from the de-acidifying chambers 5 of the electrodialysis apparatus and mixed with the corresponding suspended solids retentate. The resulting product tastes sweeter (less tart) than the original grapefruit juice and is free of any salt taste.

EXAMPLE 4:

The experiment of Example 3 is repeated except that reconstituted lemon juice is substituted for the reconstituted grapefruit juice and the AMV membranes (A) are replaced with Type ACLE-5P fouling resistant anion-selective membranes available from Tokuyama Soda Co., Tokuyama City, Japan. The direction of the electric current is reversed every 30 minutes and the flows of clear lemon juice and organic acid receiving stream are simultaneously interchanged. Approximately 10 percent citric acid is recovered from the organic acid receiving chambers. The partially de-acidified lemon juice serum from the de-acidifying chambers is mixed with the corresponding suspended solids retentate from the cross-flow filtration. The resulting product tastes less tart than the original reconstituted lemon juice and is free of any salt taste.

It will be apparent to those skilled in the art that numerous changes and modifications may be made in the preferred embodiments of the invention described above without departing from the scope of the invention. Accordingly, the whole of the foregoing description is to be construed in an illustrative and not in a limitative sense, the scope of the invention being defined solely by the appended claims.

What is claimed is:

1. A method for recovering organic acid in substantially free acid form from an aqueous solution in which, together with other organic matter, said organic acid occurs at least in part as free acid, comprising:
   (a) passing said solution through at least one de-acidifying compartment, each deacidifying compartment bounded on each face thereof by membrane surfaces substantially permeable to anions, each deacidifying compartment also having juxtaposed on one face thereof a free organic acid receiving compartment, each of said receiving compartment bounded on the face juxtaposed to said de-acidifying compartment by a membrane surface having a lower transport selectively for hydrogen ions than the membrane surface bounding said receiving compartment on the opposite face thereof, said opposite face also juxtaposed to a hydrogen ion source;

(b) passing a substantially direct electric current in series through each of said de-acidifying compartment and each of said juxtaposed free organic acid receiving compartment in a direction to cause transfer to said free organic acid receiving compartment of anions of said organic acid from said de-acidifying compartment and hydrogen ions from said hydrogen ion source.

2. The method of claim 1 wherein said aqueous solution is substantially clarified prior to passage through said de-acidifying compartments.

3. A method for decreasing the tartness of fruit juice comprising:

(a) dividing such juice into a clarified portion and a non-clarified portion;

(b) passing said clarified portion through at least one de-acidifying compartment bounded on each face therof by membrane surfaces substantially permeable to anions, each de-acidifying compartment also having juxtaposed on one face thereof a free organic acid receiving compartment, each said receiving compartment bounded on the face juxtaposed to said de-acidifying compartment by a membrane surface having a lower transport selectivity for hydrogen ions than the membrane surface bounding said receiving compartment on the opposite face thereof, said opposite face also juxtaposed to a hydrogen ion source;

(c) passing a substantially direct electric current in series through each of said de-acidifying compartment and each of said juxtaposed free organic acid receiving compartment in a direction to cause transfer into said free organic receiving compartment of anions of said organic acid from said clarified portion and of hydrogen ions;

(d) recovering from all of said de-acidifying compartments said clarified portion partly depleted of free organic acid;

(e) combining said non-clarified portion with said clarified portion partly depleted of organic acid; and (f) removing from said free-organic-acid-receiving compartments solution comprising the free organic acid of the anions of said organic acid transferred from said clarified portion.

4. The method of claim 1 or 3 wherein said direct electric current also causes transfer of hydroxide ion into said de-acidifying compartments.

* * * * *